(12) United States Patent
Aalders et al.

(10) Patent No.: US 11,439,734 B2
(45) Date of Patent: Sep. 13, 2022

(54) BREAST PUMP AND EXPRESSION KIT FOR A BREAST PUMP

(71) Applicant: KONINKLIJKE PHILIPS N.V., Eindhoven (NL)

(72) Inventors: Arnold Aalders, Eindhoven (NL); Roy Emile Beunen, Eindhoven (NL); Lauret Francisca Stulemeijer, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 349 days.

(21) Appl. No.: 15/126,093

(22) PCT Filed: Mar. 26, 2015

(86) PCT No.: PCT/EP2015/056575
§ 371 (c)(1),
(2) Date: Sep. 14, 2016

(87) PCT Pub. No.: WO2015/150225
PCT Pub. Date: Oct. 8, 2015

(65) Prior Publication Data
US 2017/0072119 A1 Mar. 16, 2017

(30) Foreign Application Priority Data
Mar. 31, 2014 (EP) .................................. 14162521

(51) Int. Cl.
*A61M 1/06* (2006.01)
*A61M 1/00* (2006.01)

(52) U.S. Cl.
CPC .............. *A61M 1/064* (2014.02); *A61M 1/06* (2013.01); *A61M 1/78* (2021.05); *A61M 1/784* (2021.05);
(Continued)

(58) Field of Classification Search
CPC ...... A61M 1/06; A61M 1/064; A61M 1/0052; A61M 1/0049; A61M 2205/7518; A61M 1/90; B01D 29/055
See application file for complete search history.

(56) References Cited

U.S. PATENT DOCUMENTS 3,862,030 A * 1/1975 Goldberg ............... B01D 17/10
210/767
4,177,149 A * 12/1979 Rosenberg ......... B01D 19/0031
210/436
(Continued)

FOREIGN PATENT DOCUMENTS

RU 2125471 C1 1/1999
WO 2005032608 A1 4/2005
(Continued)

OTHER PUBLICATIONS

Pall Versapor R Membrane Product Specification Data Sheet. Retrieved Mar. 10, 2022 from http:\\https://parafix.com/wp-content/uploads/2019/01/pall-versapor-1200r-parafix.pdf. Published Dec. 2010. (Year: 2010).*

*Primary Examiner* — Nathan R Price
*Assistant Examiner* — Justin L Zamory

(57) ABSTRACT

The present invention relates to an expression kit (2) for a breast pump (1) for extracting breast milk (101) from a human teat (102). The expression kit (2) comprises: a breast pump body (10) comprising a first pressure chamber (11) and a second pressure chamber (21); wherein the first pressure chamber (11) is configured for connection to a pressure unit (30) for generating a in the pressure chamber (11); wherein the second pressure chamber (21) comprises a breast-receiving funnel (22), a milk outlet (23) and a milk path (24) from the breast-receiving funnel (22) to the milk outlet (23); and wherein the first and the second pressure (11, 21) chamber are separated by a breathable membrane (50),
(Continued)

which is gas-permeable and liquid-impermeable, for separating the first pressure chamber (11) from liquid in the milk path (24), wherein the breathable membrane (50) is a hydrophobic membrane. Further, the present invention relates to a breast pump (1).

18 Claims, 7 Drawing Sheets

(52) U.S. Cl.
CPC . *A61M 2205/0227* (2013.01); *A61M 2205/10* (2013.01); *A61M 2205/59* (2013.01); *A61M 2205/70* (2013.01); *A61M 2205/7518* (2013.01); *A61M 2205/7536* (2013.01)

(56) References Cited

U.S. PATENT DOCUMENTS

| | | | |
|---|---|---|---|
| 4,416,993 A * | 11/1983 | McKeown | B01D 61/00 210/150 |
| 4,465,485 A * | 8/1984 | Kashmer | A61M 1/784 604/320 |
| 4,487,606 A * | 12/1984 | Leviton | A61M 1/0052 141/59 |
| 5,071,403 A * | 12/1991 | Larsson | A61M 1/06 604/320 |
| 5,171,439 A * | 12/1992 | Vakharia | B01D 19/0031 210/436 |
| 5,380,328 A * | 1/1995 | Morgan | A61B 17/8071 606/70 |
| 5,458,586 A * | 10/1995 | Adiletta | A61M 1/0049 604/326 |
| 5,636,643 A | 6/1997 | Argenta | |
| 6,383,163 B1 | 5/2002 | Kelly | |
| 6,974,439 B1 * | 12/2005 | McKendry | A61M 1/066 604/74 |
| 7,381,197 B2 | 6/2008 | Kelly | |
| 8,353,865 B2 | 1/2013 | Thilwind | |
| 8,926,556 B2 | 1/2015 | Van Eijkelenborg | |
| 9,999,736 B2 | 6/2018 | Lauer | |
| 2001/0029956 A1 * | 10/2001 | Argenta | A61M 1/0088 128/897 |
| 2003/0004459 A1 | 1/2003 | McKendry | |
| 2007/0135761 A1 | 6/2007 | Cheng | |
| 2010/0294274 A1 * | 11/2010 | Poirier | A62B 18/088 128/202.22 |
| 2012/0116299 A1 | 5/2012 | Tack | |
| 2013/0108845 A1 * | 5/2013 | Tee | B01D 71/32 428/206 |
| 2013/0213890 A1 | 8/2013 | Kelly | |
| 2015/0112298 A1 * | 4/2015 | Pirzada | A61M 1/062 604/500 |

FOREIGN PATENT DOCUMENTS

| | | |
|---|---|---|
| WO | 2008057218 A2 | 5/2008 |
| WO | 2014045159 A1 | 3/2014 |

* cited by examiner

BREAST PUMP AND EXPRESSION KIT FOR A BREAST PUMP

This application is the U.S. National Phase application under 35 U.S.C. § 371 of International Application No. PCT/EP2015/056575, filed on Mar. 26, 2015, which claims the benefit of International Application No. 14162521.0 filed on Mar. 31, 2014. These applications are hereby incorporated by reference herein.

FIELD OF THE INVENTION

The present invention relates to a breast pump for extracting breast milk from a human teat, and more specifically to an expression kit for a breast pump.

BACKGROUND OF THE INVENTION

A breast pump is a device used by mothers for expressing their breast milk into a baby-feeding bottle. The milk is typically expressed by generating a negative pressure in a vacuum chamber of the breast pump in which the teat is positioned. The part of the breast pump which is applied to the breast can be referred to as an expression kit.

For hygienic reasons, most breast pumps use a diaphragm. A non-permeable resilient silicone diaphragm acts as a hygienic shield between the breast and the vacuum pump. For creating a vacuum at the breast, the diaphragm has to make a stroke. The vacuum pump causes the diaphragm to flex thereby expanding the air in the vacuum chamber. This expansion creates the required vacuum at the breast. When the vacuum at the pump side is released, the resilient diaphragm will move to its rest position again. Since the vacuum at the vacuum pump is indirectly causing the vacuum at the breast, the hygienic function is implemented. This concept is well-established and has been used in the industry for many years.

US 2012/0116299 A1 discloses a breast pump, wherein a deformation of a non-permeable resilient silicone membrane as the diaphragm creates a negative pressure in the vacuum chamber.

WO 2014/045159 A1 discloses a further breast pump with a non-permeable deformable membrane as the diaphragm. The breast pump comprises a limiter to limit a deformation of the membrane. A stroke volume of the membrane can thus be limited.

WO 2008/057218 A2 discloses a further conventional breast pump with a non-permeable resilient diaphragm as a barrier which prevents contamination from entering a vacuum pump air line.

Since the diaphragm has to make a stroke for creating the vacuum at the breast, a large air volume is required. The stroke can only be made when there is a sufficiently large air volume available in the breast pump for the displacement of the diaphragm. Thus, the required air volume limits the minimum size of the breast pump.

U.S. Pat. No. 5,071,403 relates to protecting the pump of a breast pump from fouling by milk. Air being drawn toward the vacuum pump passes through a porous body disposed in an air passage interconnecting the vacuum pump and a breast-contacting hood. When milk reaches the porous body and wets it, air may no longer pass through the porous body at least where the porous body is wet. Depending upon the extent of contact of milk with the porous body, the amount of vacuum that reaches an interior of the breast-receiving hood is reduced or eliminated, thereby reducing or eliminating further expression of milk. The continued flow of air to the vacuum pump is reduced or halted in order to protect the pump. Hence, the hydrophilic porous body serves as a barrier across a vacuum line that protects the pump.

US 2003/004459 A1 discloses a breast pump with an optional hydrophilic filter for added isolation of the vacuum pump and vacuum lines.

US 2007/135761 A1 discloses a breast pump with a liquid crystal display which can display information about the usage of the breast pump such as volume of milk pumped.

SUMMARY OF THE INVENTION

It is an object of the present invention to provide a more compact expression kit, while keeping the vacuum pressure at the breast unchanged compared to conventional breast pumps. It is a further object to provide hygienic function of the expression kit and breast pump, in particular in rental and/or hospital use.

In a first aspect of the present invention an expression kit for a breast pump for extracting breast milk from a human teat is presented, the expression kit comprising:
a breast pump body comprising a first pressure chamber and a second pressure chamber,
wherein the first pressure chamber is configured for connection to a pressure unit for generating a pressure in the first pressure chamber,
wherein the second pressure chamber comprises a breast-receiving funnel, a milk outlet and a milk path from the breast-receiving funnel to the milk outlet, and
wherein the first and the second pressure chamber are separated by a breathable membrane, which is gas-permeable and liquid-impermeable, for separating the first pressure chamber from liquid in the milk path, wherein the breathable membrane is a hydrophobic membrane.

In a further aspect of the invention a breast pump for extracting breast milk from a human teat is presented, the breast pump comprising:
an expression kit as described above, and
a pressure unit for generating a pressure.

Preferred embodiments of the invention are defined in the dependent claims. It shall be understood that the claimed breast pump has similar and/or identical preferred embodiments as the claimed expression kit and as defined in the dependent claims.

Instead of using a non-permeable silicone diaphragm according to the prior art, it is suggested to use a breathable membrane, which is gas-permeable and liquid-impermeable for separating the first pressure chamber from the milk path. The inventors thereby break with the well-established concept of strictly separating breast and pressure unit with a diaphragm which is impermeable for gas and liquid.

When a woman's breast is placed in the breast-receiving funnel, that opening of the second pressure chamber is sealed closed. Accordingly, when a milk receptacle such as a baby-feeding bottle is connected to the milk outlet, that opening of the second pressure chamber is sealed closed. The skilled person will appreciate that the term sealed in this context is not limited to hermetically sealed but also allows a minor leakage as long as the breast milk can be extracted. The breast-receiving funnel is in fluid communication with the milk outlet via the milk path.

In operation, the pressure unit may generate a pressure, for example a negative pressure or vacuum, in the first pressure chamber. Due to the breathable membrane between the first pressure chamber and the second pressure chamber, this causes a corresponding vacuum in the second pressure chamber for extracting breast milk from the teat. If the negative pressure at the first pressure chamber is released, this causes a corresponding pressure in the second pressure chamber. For example, a sequence of vacuum and ambient pressure can mimic the sucking motion of a baby and stimulate lactation. Since the breathable membrane is permeable to air, a negative pressure can be generated in the second vacuum chamber without having to move a diaphragm. Hence, the space requirement reduces significantly.

In other words, there is no need for providing an air volume in the breast pump body for a movement of the resilient diaphragm. The volume for the movement of the resilient diaphragm is also referred to as 'dead volume'. Hence, the dead volume for displacing the flexible silicone membrane can be omitted. As a first advantage, this increases the design freedom and enables a breast pump with reduced size and improved handling. As a second advantage, the air volume which has to be displaced by the pressure unit reduces and thus a smaller and less expensive pressure unit can be used.

Furthermore, in contrast to conventional breast pumps, wherein a resilient silicone diaphragm has to be flexed, i.e., a significant amount of pump power is required for overcoming a spring force of the silicone diaphragm, the breathable membrane can provide a lower resistance for the pressure unit. This further supports the use of a smaller and less expensive pressure unit.

It should be noted that a silicone diaphragm for conventional breast pumps can be made in different hardnesses and shapes. All will have different elastic behaviors but all designs will require an optimization of the design to allow for a small pressure drop. A large area membrane allows for relatively small pressure drop across the diaphragm but will require a large diameter somewhere in the product, thereby limiting the design of the product. A smaller area will lead to more design freedom but to a larger pressure drop. This pressure drop will demand a more powerful vacuum pump. A more powerful vacuum pump, however, will be larger and/or more expensive. In contrast to the prior art, the solution according an aspect of to the present invention allows for a very small pressure drop and allows both a more compact and less expensive expression kit and breast pump.

Furthermore, the breathable membrane according an aspect of the present invention can be mounted in all kinds of shapes, such as single or double curved surfaces, while a moving diaphragm according to the prior art needs specific shapes in order to work efficiently.

As a further advantage, since the flexible, bending diaphragm is omitted, a cleanability of the breast pump body can be improved. This is particularly advantageous for small sized expression kits, where conventionally a corrugated or folded diaphragm is employed. In other words, the resilient silicone diaphragm in conventional breast pumps may include a bellows section which is deformed when the resilient diaphragm is moved up and down in the pumping process. A bellows section can be necessary to provide sufficient flexing capability of the diaphragm. An advantage of the breathable membrane according to an aspect of the present invention is that the breathable membrane does not have to be deformed. This avoids the bellows section or corrugated section and thereby simplifies a cleaning process of the membrane. In other words, the breathable membrane can be a planar, partially planar or substantially planar membrane and thus simplify the cleaning process.

Further advantageously, the expression kit comprises the breast pump body, with the first pressure chamber and the second pressure chamber, and the breathable membrane in-between the pressure chambers as one entity. Thereby, the number of entities can be reduced and a handling of the breast pump can be simplified.

As used herein, the term 'breathable membrane', refers to a membrane which is breathable in that gases pass whereas liquids do not. The breathable membrane can also be referred to as a semipermeable membrane. For example, it can breathe air but does not pass milk and/or water. Main parameters for choosing a breathable membrane comprise, for example, required flow, required pressure drop over the membrane (membrane air-restriction), bio-compatibility, sterilization/cleaning properties, mounting to a carrier material such as lasering, gluing, ultrasonic welding and the like.

The breathable membrane according to an aspect of the present invention is a hydrophobic membrane. An advantage of a hydrophobic membrane is that it repels water and breast milk. Droplets of water and/or breast milk can clear off the membrane automatically. This ensures that a sufficient area of the breathable membrane is available for gas exchange between the first and the second pressure chamber. Hence, the size of the breathable membrane can be reduced compared with a non-hydrophobic or hydrophilic breathable membrane. In contrast to a membrane that can be wetted, there is no need to provide a large surface area with some added safety margin. In order to provide a sufficient gas volume flow, a safety margin would be required in case some of the surface area would be blocked by droplets. A low pressure drop across a membrane of a given surface area can thus be provided also when droplets of water and/or milk reach the breathable membrane. Advantageously, the breathable membrane is a hydrophobic porous membrane for allowing air to pass but which does not allow water or milk to pass. Hence, no droplets reach the first pressure chamber.

Further, the inventors have found that being hydrophobic positively influences bacteria-retention and can prevent that bacteria are transferred to the vacuum tube and pump. Hence, the hygienic function can be improved, in particular for rental or hospital use. Due to the hydrophobic property and thus the milk repellent behavior of the hydrophobic breathable membrane, the time of contact between the milk and the breathable membrane can be reduced. Thereby, the likelihood of transferring germs and bacteria, which are carried by the milk towards the breathable membrane and further on to pump and vacuum line can be further reduced.

As a further advantage, a hydrophobic breathable membrane positively influences the liquid-impermeable behavior. Due to the hydrophobic property and liquid repellent behavior, the requirements regarding liquid impermeability are reduced. Hence, for example, a thinner membrane or a membrane with larger pore diameter can be used while still maintaining an overall liquid-impermeable behavior at typical pressures of a breast pump. Thereby, a lower pressure drop across the membrane can be realized such that a smaller area and thus more compact membrane can be used and/or a lower pump power is required.

Advantageously, the hydrophobic behavior is tuned to the application.

Advantageously, the breathable membrane is a bacteria-retentive hydrophobic breathable membrane. Methods used to determine bacterial retention are described in the ASTM standards. Bacterial retention in a filter used for liquid filtration can be determined as described in the standard ASTM F838-05(2013) "Standard Test Method for Determining Bacterial Retention of Membrane Filters Utilized for Liquid Filtration".

In a further refinement, the hydrophobic breathable membrane is bacteria-retentive in an aerosol environment. An aerosol can be considered as a mixture, in particular a colloid, of fine solid particles or liquid droplets, in air or another gas. While the prior art focuses on preventing milk as a liquid from reaching the vacuum pump, the inventors have realized that aerosol components should also be taken into account. Due to the vacuum pressure, the transfer from liquid phase into gaseous phase is fostered such that undesired components could pass a breathable membrane in this state even though the membrane is liquid-impermeable. In particular, germs such as bacteria could potentially be transferred past a liquid-impermeable but gas-permeable membrane. It is therefore suggested to use a hydrophobic breathable membrane, wherein the breathable membrane is a bacteria-retentive membrane, which is bacteria-retentive in an aerosol environment. Bacteria retention in an aerosol environment can be determined by BFE (bacterial filtration efficiency) testing as described in the standard ASTM F2101-14 "Standard Test Method for Evaluating the Bacterial Filtration Efficiency (BFE) of Medical Face Mask Materials, Using a Biological Aerosol of *Staphylococcus Aureus*".

In an embodiment, the breathable membrane (50) comprises a hybrid membrane structure comprising both a woven and non-woven membrane structure. An advantage of this embodiment is that the advantages of woven and non-woven materials can be combined. For example, a woven layer can be arranged on top of a non-woven layer. The woven layer can face the second pressure chamber. The non-woven layer can face the first pressure chamber. The woven layer can be liquid-impermeable and thereby prevents milk from passing the breathable membrane as a first membrane stage. An advantage of a woven layer can be its tribo-electrical properties. As a second membrane stage, the non-woven layer can be bacteria retentive in an aerosol environment. An advantage of the non-woven layer is that a non-woven layer can provide a low resistance with high efficiency.

In an embodiment, the breathable membrane comprises a hydrophobic backing. A backing refers to a support layer, in particular a stiff support layer, of the breathable membrane. Advantageously, the hydrophobic backing faces the second pressure chamber. The use of a hydrophobic backing can prevent liquids to come into contact with an additional layer of the breathable membrane. Hence, a hydrophobic backing can advantageously be combined with one or more further in particular high efficiency membrane layers, wherein the additional layers can also be non-hydrophobic.

In an embodiment, the breathable membrane is gas-permeable and liquid-impermeable in both directions. In other words, gases can pass from the first pressure chamber to the second pressure chamber and from the second pressure chamber to the first pressure chamber, whereas liquids are blocked in both directions. In contrast to a one-way permeable membrane, such a two-way breathable membrane avoids a continuous build-up of vacuum pressure at the breast and teat which may cause discomfort to the user.

In an embodiment, at least a portion of the breathable membrane is arranged at an angle with respect to the milk outlet. Advantageously, the breathable membrane is thereby arranged at an angle with respect to a horizontal plane when the expression kit is applied to the human teat. In other words, the breathable membrane is in a non-horizontal orientation during typical use of the expression kit. The angle can be determined with respect to a plane of the milk outlet, wherein the plane of the milk outlet can correspond to a plane in which a rim of a milk receptacle is located when the milk receptacle is connected to the breast pump body. An advantage of this embodiment is that droplets of milk and/or water can clear off the membrane automatically since they are drawn away by gravity. In a further refinement, the breathable membrane comprises sub-sections wherein the sub-sections of the breathable membrane are arranged at an angle with respect to each other. This ensures that at least a sub-section of the breathable membrane is arranged in a non-horizontal orientation when the breast pump is used. For example, a pyramid shape or free form that is partially non-horizontal can be used.

In an embodiment, the breathable membrane comprises one or more of polyethylene, polypropylene, polybutylene terephthalate (PBT), polytetrafluoroethylene or expanded polytetrafluoroethylene. In a further embodiment, the breathable membrane consists of polyethylene, polypropylene, polybutylene terephthalate (PBT) polytetrafluoroethylene and/or expanded polytetrafluoroethylene. An advantage of a breathable membrane made of such material is that it can be manufactured at reasonable cost. Furthermore, the material can be designed to withstand the expected cleaning procedures including manual washing, dishwasher, hot water and the like with or without detergents, but it can also be capable of the withstanding hospital kind of cleaning techniques such as Gamma, ETO, Autoclave Sterilization and disinfection methods.

In an embodiment the breathable membrane is configured as a hygienic shield. Advantageously, the properties of the breathable membrane go beyond merely being gas-permeable and liquid-impermeable, but further accomplish a hygienic shielding function. For example, this can be implemented by choosing a porous material wherein the structure and/or size of the porous openings prevents undesired components, for example germs, to pass. Alternatively or in addition, a thickness of the membrane is chosen accordingly.

In an embodiment the expression kit further comprises a support structure for supporting the breathable membrane. The support structure can be implemented as an integral part of the membrane, as a separate dedicated element or as a part of the breast pump body. In other words, the support structure serves as a carrier for the breathable membrane. The support structure can be configured to provide mechanical stability, in particular for preventing the membrane from unduly flexing due to the applied pressure. For example, the support structure can be a rigid structure such as a mesh structure. Advantageously, the support structure is implemented at a side of the breathable membrane which faces the first pressure chamber such that the support structure does not come into contact with the milk path. Thereby, the support structure is easier to clean. Further advantageously, the support structure provides better handling of the breathable membrane. Further advantageously, the support structure also protects the membrane from damage by the user.

In an embodiment, the expression kit further comprises a seal arranged between the breathable membrane and the breast pump body. For example, the seal is a seal ring around the breathable membrane which is configured to prevent leakage, in particular liquid leakage, between the first vacuum chamber and the second vacuum chamber. In an embodiment, the breathable membrane comprises a seal ring with a silicone seal for sealing, a hard plastic ring as a support structure. An advantage of this embodiment is that the breathable membrane including seal and support structure can be separated from the breast pump body for easy cleaning. In an alternative embodiment, the breathable membrane is directly fixed to the pump body and thereby prevents leakage. An advantage of this embodiment is the very low amount of materials used and thus a reduced manufacturing cost.

In an embodiment, the expression kit further comprises a wear indicator for indicating a wear of the expression kit, in particular of the breathable membrane. An advantage is that the wear indicator indicates how often the device has been used. Thus, the wear indicator can indicate when it is time, for example, to replace the breathable membrane or a seal. The wear indicator can be implemented as a counter, a counter which is manually operated or, for example, as a color that fades over time such as a blue color indicator.

In an embodiment, the expression kit further comprises a restrictor for reducing a surface area of the breathable membrane. In other words, a resistance provided by the breathable membrane can be tuned for example by reducing the surface area of the breathable membrane. The restrictor can thus be used to tune an effective surface area of the breathable membrane. A small surface area of the breathable membrane can lead to a slower build-up of the pressure in the second pressure chamber. Hence, as an alternative to controlling the pressure unit, a mechanical restrictor can be used. Thereby, a simpler and less expensive pressure unit can be used. The use of a restrictor is also advantageous for manual breast pumps, wherein one and the same pumping mechanism can be used for providing different pressure situations at the breast, as desired by the woman, by simply choosing an appropriate restrictor. Alternatively, the restrictor is an integral part of the membrane which defines a resistance the membrane exerts to the gas volume flow from the first pressure chamber to the second pressure chamber or from the second pressure chamber to the first pressure chamber.

In an embodiment, the expression kit further comprises a splash guard arranged between the milk path and the breathable membrane. An advantage of this embodiment is that the splash guard acts as an additional shield for preventing breast milk to reach the breathable membrane. Hence, the splash guard avoids that a substantial part of the breathable membrane is covered with liquid and thus not capable of passing a sufficient amount of air anymore.

In an embodiment at least one of the first pressure chamber and the second pressure chamber is configured to enable access to the breathable membrane. An advantage of this embodiment is that it provides easy access for cleaning purposes. For example, the second pressure chamber of the breast pump body may comprises a lid that can be opened and provide access to the breathable membrane for cleaning and/or for removing the breathable membrane. Alternatively or in addition, access can be provided from the second pressure chamber. An optional splash guard can be implemented as a flexible element which can be removed or pushed aside for cleaning.

In an embodiment the expression kit further comprises a milk receptacle for connection to the milk outlet. The expression kit may comprise a fitting to enable a receptacle such as a milk-collection bottle having a co-operating fitting to be coupled to the breast pump body. Alternatively, the milk receptacle forms part of the breast pump body. Advantageously, the milk flows into the receptacle or storage container by gravity. The second vacuum chamber can be sealed by the milk receptacle. Alternatively, or in addition, the milk outlet further comprises a one-way valve to allow expressed milk to exit the second pressure chamber but to prevent air from entering the second pressure chamber through the milk outlet.

The pressure unit can be a manual or electric pump which is arranged directly at the expression kit or at a remote location. The pressure unit is configured for connection to the first pressure chamber. A remote pressure unit can be connected to the first pressure chamber by a tube system. Hence, the expression kit can optionally comprise a tube system for connection to a remote vacuum unit.

As used herein, the term 'negative pressure' or 'vacuum' refers to a negative pressure with respect to ambient pressure.

The expression kit as described above enables the design of a more compact expression kit, because a large volume for the diaphragm to make a stroke for creating the vacuum at the breast is no longer required. A more compact expression kit and a smaller volume to be pressurized allow the appliance of a smaller pressure unit having reduced power. A smaller pressure unit is generally less expensive. Furthermore, with the appliance of a membrane the hygienic function is maintained since the breathable membrane is impermeable to breast milk, such that the pressure unit is separated from the milk path between the breast-receiving funnel and the milk outlet.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
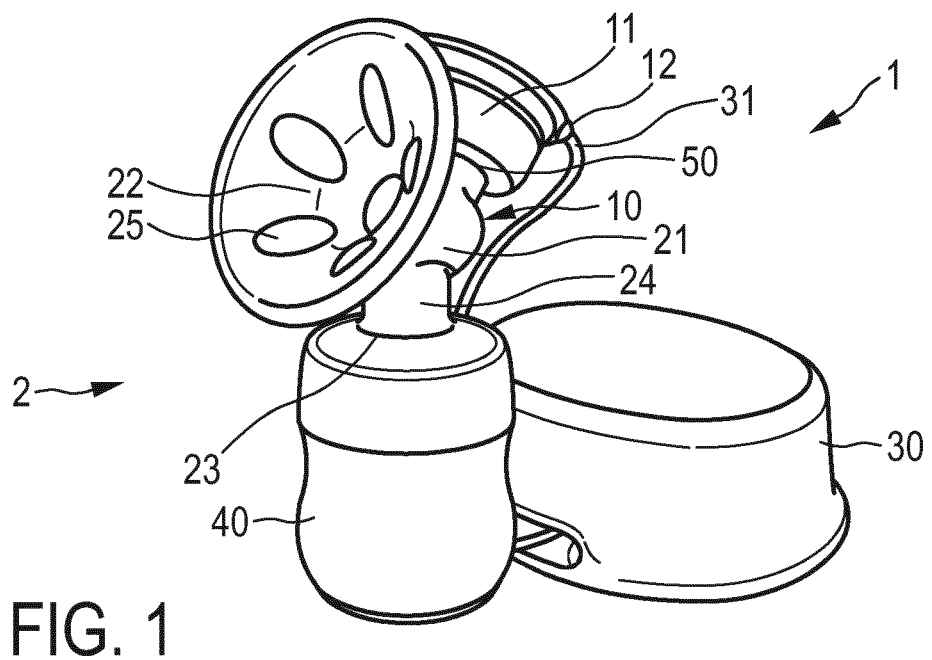
FIG. 1 shows a perspective view of a first embodiment of a breast pump.

FIG. 1 shows an embodiment of a breast pump 1 comprising an expression kit 2 and a pressure unit 30 for generating a pressure, for example a negative pressure or vacuum (thus the pressure unit 30 is sometimes referred to below as vacuum unit 30). The expression kit 2 comprises a breast pump body 10 and a milk receptacle 40 in form of a baby-feeding bottle. The breast pump body 10 is a body, which is part of expression kit 2 of the breast pump 1. In this embodiment, the pressure unit 30 is an electric vacuum unit. Alternatively, a manual pressure unit or pump can be used. The electric vacuum unit 30 is connected to the breast pump body 10 via a tube 31. The electric vacuum unit 30 can thus be arranged at a remote location for reducing the size of that part of the breast pump 1 which is to be applied to a woman's breast. Alternatively, the vacuum unit can be directly arranged at the breast pump body 10 of the expression kit 2, as for example shown in US 2012/0116299 A1.

The expression kit 2 comprises a breast pump body 10 having a first pressure chamber 11 and a second pressure chamber 21. In this embodiment, the pressure chambers can also be referred to as vacuum chambers. The first pressure chamber 11 is configured for connection to the vacuum unit 30 via a connector 12 for connection to the tube 31 to the electric vacuum unit 30.

It should be noted that a plurality of expression kits 2 can share a common pressure unit 30, for example for expressing milk from both teats at the same time.

The second pressure chamber 21 comprises a breast-receiving funnel 22, a milk outlet 23 and a milk path 24 from the breast-receiving funnel 22 to the milk outlet 23. The breast-receiving funnel 22 is thus in fluid communication with the milk outlet 23 via the milk path 24. The breast-receiving funnel 22 can further comprise a massage cushion 25 being designed to feel soft and warm and imitating a baby's sucking action to provide fast milk flow quietly, comfortably and gently.

The first pressure chamber 11 and the second pressure chamber 21 are separated by a hydrophobic breathable membrane 50. The hydrophobic breathable membrane 50 is gas-permeable and liquid-impermeable and separates the first pressure chamber 11 from the milk path 24 in the second pressure chamber 21. The hydrophobic breathable membrane 50 is a hydrophobic breathable membrane.

Figure 2:
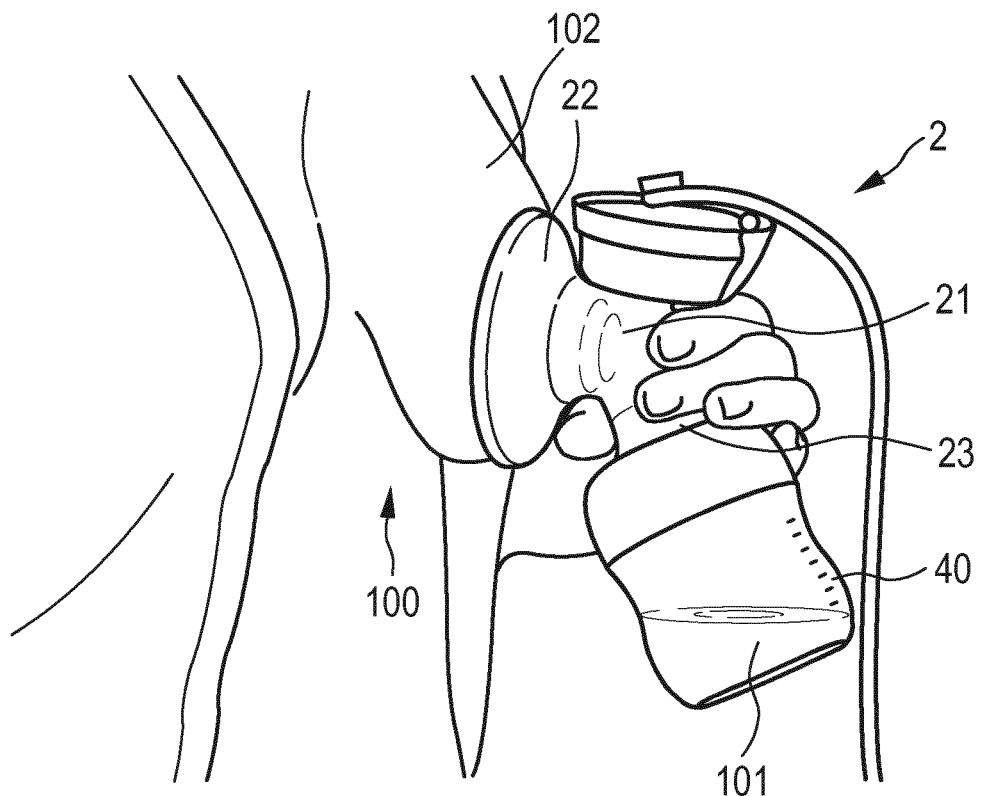
FIG. 2 shows the breast pump during application.

FIG. 2 shows the application of the breast pump 1 extracting breast milk 101 from the breast 102 of a woman 100 during typical use of the expression kit 2. When a woman's breast 102 is placed in the breast-receiving funnel 22 of the expression kit 2, that opening of the second pressure chamber 21 is sealed closed. Correspondingly, the milk outlet 23 of the second pressure chamber 21 is sealed closed by the milk receptacle 40.

Figure 3:
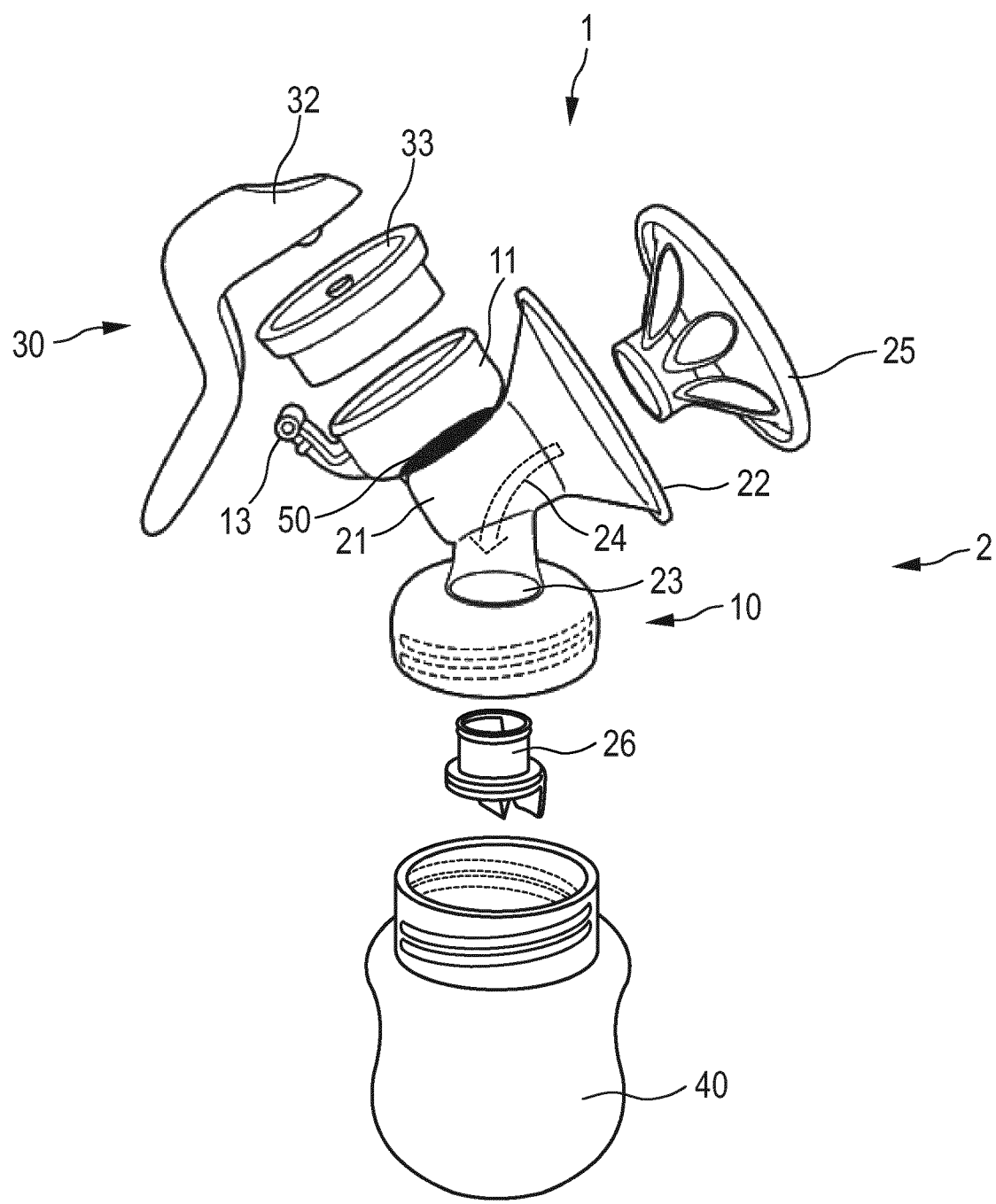
FIG. 3 shows an exploded view of a second embodiment of a breast pump.

FIG. 3 shows a further embodiment of a breast pump 1 according to an aspect of the present invention. The breast pump 1 is configured for manual operation. The breast pump 1 comprises an expression kit 2 comprising a breast pump body 10 comprising a first pressure chamber 11 and a second pressure chamber 21. The first pressure chamber 11 is configured for connection to a pressure unit 30 for generating a pressure in the first pressure chamber 11.

Instead of using an electric pressure unit as shown in FIG. 1, in this embodiment the pressure unit 30 is a manual pressure unit comprising a handle 32 and a piston 33. The handle 32 engages with the joint 13 arranged at the breast pump body 10. Operation of the handle 32 of the pressure unit 30 thereby causes an up and down movement of the piston 33 in the first pressure chamber 11 and thereby displaces the air volume in the first pressure chamber 11. It should be noted that a piston pump requires less space than a conventional diaphragm pump and thus enables a more compact design. Alternative means for generating a pressure in the first pressure chamber 11 can also be used.

The second pressure chamber 21 comprises a breast-receiving funnel 22 which can optionally be equipped with a massage cushion 25 for improved user comfort. The second pressure chamber 21 further comprises an aperture acting as the milk outlet 23. Optionally, a one-way valve 26 is arranged at the milk outlet 23. The one-way valve is configured to let milk pass from the second pressure chamber 21 to the milk receptacle 40. The milk receptacle 40 is connectable to the bottom of the breast pump body 10, e.g. by screwing, and thereby closes the lower end of the second pressure chamber 21.

The first and the second pressure chamber 11, 21 are separated by a hydrophobic breathable membrane 50, which is gas-permeable and liquid-impermeable, for separating the first pressure chamber 11 from the milk path 24 from the breast-receiving funnel 22 to the aperture of the milk outlet 23. Optionally, the hydrophobic breathable membrane 50 is fixed to the breast pump body 10. This reduces the number of parts to be handled and thereby reduces handling errors.

Exemplary embodiments of the hydrophobic breathable membrane 50 will be described in more detail with reference to FIGS. 6, 7a and 7b further below.

Figure 4:
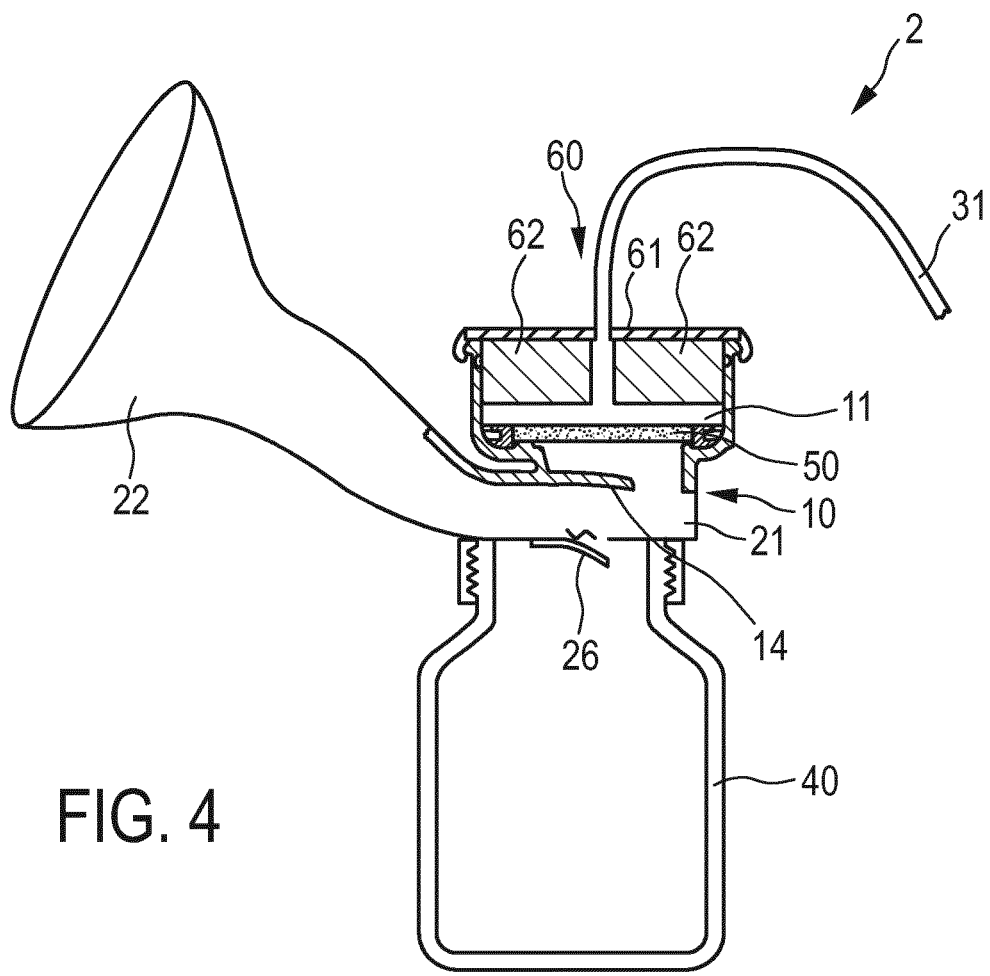
FIG. 4 shows an expression kit according to a third embodiment.

FIG. 4 shows a third embodiment of an expression kit 2 comprising a breast pump body 10 having a first pressure chamber 11 and a second pressure chamber 21. The first pressure chamber is configured for connection to a remote pressure unit via a tube 31.

In an advantageous refinement, the elements are configured for retrofitting a conventional diaphragm-based breast pump body as for example known from the breast pump model Philips Avent SCF334/02.

The first and the second pressure chamber 11, 21 are separated by a hydrophobic breathable membrane 50, which is gas-permeable and liquid-impermeable, for separating the first pressure chamber 11 and the second pressure chamber 21. For example, a vacuum applied to the first pressure chamber 11 also causes vacuum in the second pressure chamber 21 since air can pass, whereas water and/or milk in the second pressure chamber are blocked. Thereby, the hydrophobic breathable membrane 50 acts as a hygienic shield. Being hydrophobic further positively influences the bacteria-retention and prevents that bacteria are transferred to the vacuum tube 31 and pump.

The second pressure chamber 21 again comprises a breast-receiving funnel 22, a milk outlet 23 and a milk path 24 from the breast-receiving funnel 22 to the milk outlet 23. In the shown embodiment, the milk outlet 23 is equipped with an optional alternative embodiment of a one-way valve 26 in form of a flap.

The breast pump body 10 comprises an optional splash guard 14 arranged in the second pressure chamber 21 for shielding the breathable membrane 50 from droplets of breast milk. Thereby, the splash guard 14 can act as a first barrier which avoids that too much breast milk reaches the hydrophobic breathable membrane 50. Droplets of milk can clear off the hydrophobic breathable membrane 50 automatically.

An interface assembly 60 is arranged in the first pressure chamber 11 and configured for providing connection to the vacuum unit via the tube 31. The interface assembly 60 comprises a lid 61 for sealing the first pressure chamber 11. Advantageously, the interface assembly 60 of the expression kit further comprises one or more volume-reduction elements 62, which reduce the dead air volume in the first pressure chamber 11. Thereby, the air volume which has to be evacuated is significantly reduced. Thus, a smaller and/or less expensive vacuum unit can be used.

In an alternative embodiment, when there is no need for compatibility with existing breast pump bodies, the volume of the first pressure chamber 11 can be reduced by design. This is possible since there is no need for a diaphragm to perform a stroke.

In the embodiment shown in FIG. 4, a diameter of an upper portion of the first pressure chamber 11 is larger or equal to a diameter of the hydrophobic breathable membrane 50. The first pressure chamber 11 is thus configured to enable access to the hydrophobic breathable membrane 50 when the interface assembly 60 is removed. An advantage of this embodiment is easy access to the breathable membrane 50 for cleaning or replacement.

Figure 6:
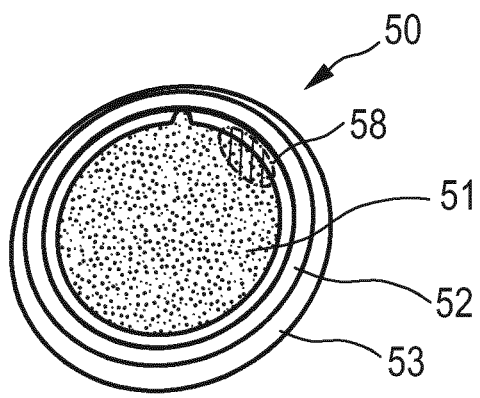
FIG. 6 shows an embodiment of a breathable membrane.

FIG. 6 shows an embodiment of a hydrophobic breathable membrane 50 in more detail. The breathable membrane 50 comprises a breathable central membrane portion 51 which is gas-permeable and liquid-impermeable. A support structure in form of a rigid ring 52 can be arranged at a perimeter of the breathable central membrane portion 51 for providing mechanical stability. Optionally, the rigid ring 52 is configured as a restrictor for limiting the surface area of the breathable central membrane portion 51 to a desired area.

Furthermore, a seal 53 such as a silicone seal can be provided as a seal to a wall of the breast pump body 10, for example to avoid leakage. It should be noted that the seal does not necessarily have to be air tight as long as it prevents breast milk from flowing from the second pressure chamber to the first pressure chamber. An optional wear indicator 58 indicates a wear of the hydrophobic breathable membrane 50, including the seal 53, and thereby indicates when it is time to replace the hydrophobic breathable membrane 50.

Figure 7A:
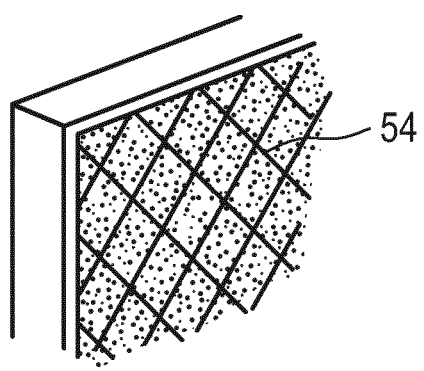
FIGS. 7A and 7B show further embodiments of a breathable membrane.
Figure 7B:
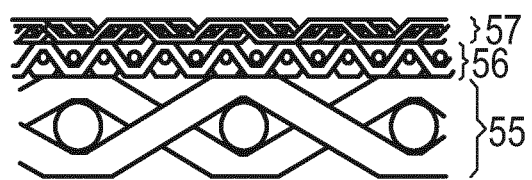

FIGS. 7A and 7B show alternative structures for providing mechanical stability to the breathable membrane 50.

In the embodiment shown in FIG. 7A, a mesh structure 54, for example made from a hard plastic or metal, is provided at one or both surfaces of the hydrophobic breathable membrane 50. Advantageously, the support structure is arranged at the side of the breathable membrane 50 which faces the first vacuum chamber for easier cleaning.

In the alternative embodiment shown in FIG. 7B, the hydrophobic breathable membrane 50 can comprise a carrier layer 55 that is much stronger and/or stiffer than the sub layers 56 and 57 which ensure that the membrane is breathable. The permeability of the sub layers 56 and 57 is adjusted to be gas-permeable and liquid-impermeable by selecting an appropriate mesh structure and/or layer thickness. At least one of the layers is hydrophobic. For example, carrier layer 55 and/or sub-layer 56 are hydrophobic and face the second pressure chamber wherein sub-layer 57 does not have to be hydrophobic. Instead of a mesh structure an alternative porous structure can be used such as a non-woven structure. A hybrid membrane structure comprising both a woven and a non-woven structure can be used. For example sub-layer 56 is a woven, hydrophobic structure, wherein sub-layer 57 is a non-woven structure.

In an embodiment, the pore size together with the thickness of the membrane achieves the desired hygienic function. In an embodiment, the pore size is less than 1 µm, in particular less than 500 nm, in particular less than 100 nm. An advantage of this embodiment is that germs such as bacteria can be blocked. Advantageously, the pore size is not only an average value but all pores are smaller than the specified pore size in order to prevent germs to pass somewhere in the membrane.

In an embodiment two sub layers 56, 57, having a first pore size, for example 1 µm, are stacked to achieve a membrane with an apparent or effective pore size being smaller than the first pore size. The pore sizes of the sub-layers 56, 57 can be the same or different.

Optionally, a further support layer is arranged on top of layer 57 for protection of the breathable membrane in FIG. 7B. Advantageously, the support structure also protects the membrane from damage by the user, for example during the cleaning process.

Figure 5:
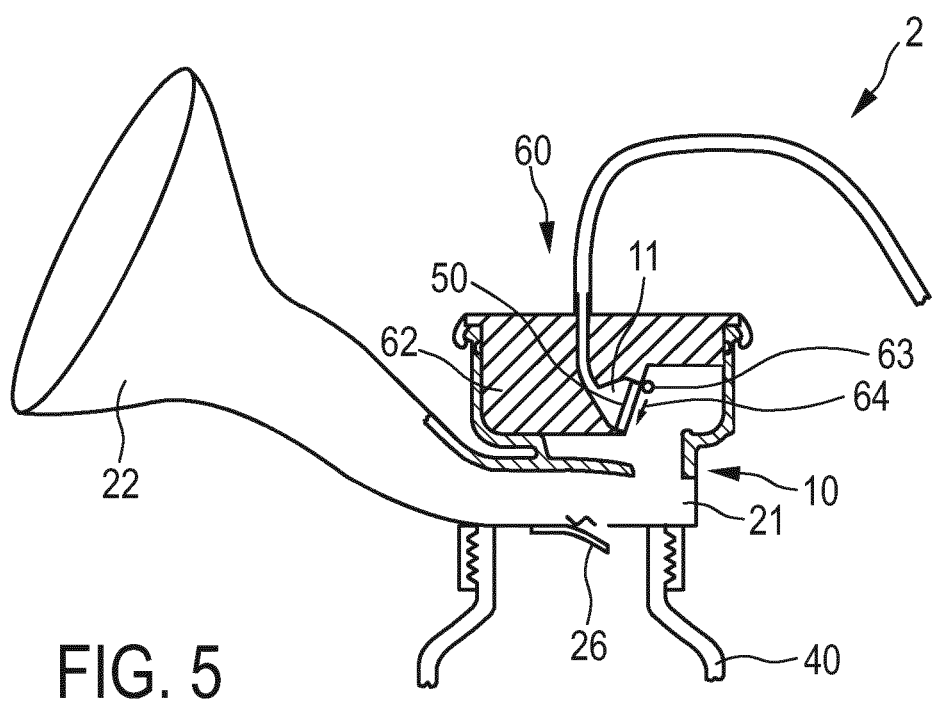
FIG. 5 shows an expression kit according to a fourth embodiment.
Figure 8:
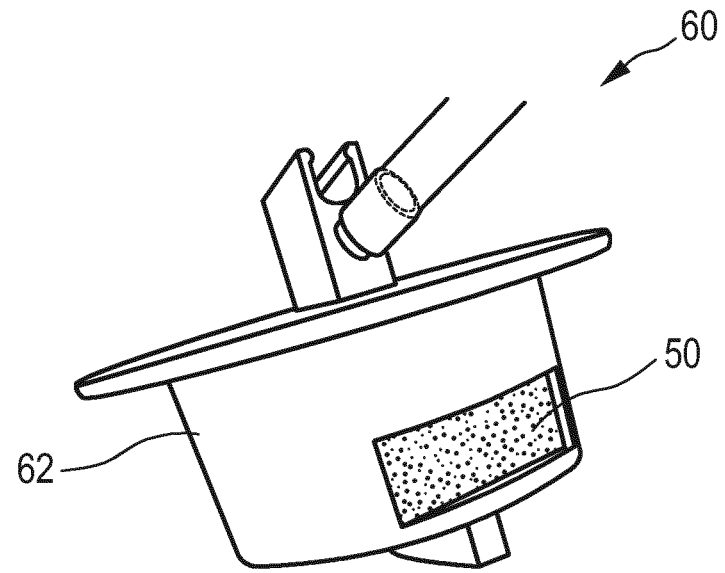
FIG. 8 shows a perspective view of an embodiment of an interface assembly.

FIG. 5 shows an embodiment of an expression kit which is based on FIG. 4. FIG. 5 illustrates an alternative interface assembly 60. In this embodiment, the interface assembly 60 of the expression kit 2 comprises the first pressure chamber 11 and the hydrophobic breathable membrane 50. For example, the interface assembly 60 can be fabricated as a silicone interface assembly which optionally also seals a top portion of the breast pump body 10. Optionally the hydrophobic breathable membrane 50 can be removed, for example for cleaning. A cross-section of the interface assembly 60 is shown in FIG. 5. A perspective view of the interface assembly 60 is shown in FIG. 8.

The interface assembly 60 is optionally configured for retrofitting a conventional breast pump body 10 and comprises an optional volume-reduction element 62 for reducing the dead volume of the breast pump body 10. In this case, a volume of the second pressure chamber 21 can be reduced.

Advantageously, as shown with reference to FIG. 5, the breathable membrane 50 is arranged non-horizontally and thereby enables milk droplets 63 to roll down due to gravity, as indicated by arrow 64. In other words, the hydrophobic breathable membrane 50 is arranged at an angle with respect to a horizontal plane when the expression kit 2 is applied to the human teat. Thus, if a milk droplet 63 of breast milk manages to reach the breathable membrane 50, the milk droplet 63 will clear automatically. Advantageously, the hydrophobic breathable membrane 50 is made from a hydrophobic material which further supports the rolling off of any milk droplets 63.

Even though the membrane is breathable, the membrane provides a pneumatic restriction to the gas volume flow. The pneumatic restriction, the surface area of the membrane and the power of the pressure unit are aligned in order to enable a desired gas volume flow. In particular, the breathable membrane has a pneumatic restriction that is low enough to enable breast pump function. For example, the pneumatic restriction is selected such that, using a vacuum pump that can deliver a free flow of e.g. 0.3 liters per minute and that has an end vacuum of e.g. −1000 mbar, a small volume of 15 ml can be evacuated to −333 mbar in approximately 1.2 seconds. When the first pressure chamber has a minimal volume, a delta pressure of 1000 mbar will be put across the breathable membrane almost immediately. The exemplary volume of the second pressure chamber of 15 ml is small, however, in general the skilled person will reduce the volume of the first and/or second pressure chamber further in order to enable the use of a small, cheap and/or energy efficient pressure unit. The values are to be understood as exemplary values for a breast pump. The skilled person will appreciate that generally other values can be selected which enable the extraction of breast milk.

In view of the foregoing, the breathable membrane with its pneumatic restriction can be specified in that the membrane provides a flow of e.g. at least 0.3 liters per minute when a pressure difference over the membrane of e.g. −1000 mbar is applied and the membrane has a predetermined surface area. These parameters enable the skilled person to determine the required flow parameter Q of the breathable membrane and select the membrane accordingly. The flow parameter Q can be defined as Q=flow through the membrane/(surface area of the membrane×pressure difference over the membrane). For a breast pump, the surface area is preferably as small as possible. A further advantage of a small membrane can be low material costs. In an advantageous embodiment, the surface area is less than 2827 $mm^2$, corresponding to a disk-shaped area having a radius of 30 mm, in particular less than 707 $mm^2$, corresponding to a disk-shaped area having a radius of 15 mm.

In view of the pneumatic restriction and a maximum membrane surface area a suitable membrane can be determined.

A desired pressure profile, i.e. a time-variant pressure, can be applied to the woman's breast using a suitable pressure unit and taking into account the pneumatic restriction of the breathable membrane.

A pneumatic restriction or resistance requirement of the hydrophobic breathable membrane can be determined via calculation. An air speed v[m/s] through the membrane can be determined via a required vacuum profile, i.e., dP/t in a certain volume. A pressure drop over the membrane (dP) is advantageously kept as low as possible, e.g. less than 100 mbar, in particular less than 50 mbar, in particular less than 20 mbar, to enable the use of a low power and compact pump (as well as low stresses in the membrane). Advantageously, a surface area is also kept as low as possible to ensure e.g. design freedom, reduce a risk of damage, improve cost efficiency and the like. For example, the membrane is a substantially circular membrane having a diameter of about 20 mm and a surface area of about 350 mm². Based thereon, a maximum resistance that is allowed for the membrane can be calculated by:

$$dP[Pa]=R[Pas/kg]\cdot q[kg/s]$$

$$q[kg/s]=v[m/s]\cdot A[m^2]\cdot rho[kg/m^3]$$

$$R[Pas]=(dP[Pa]/A[m^2])\cdot(1/v[m/s])\cdot(1/rho[kg/m^3])$$

The determination of the membrane characteristics can thus be based on this maximum resistance R as well as the retention requirements of the membrane such as bacteria retention (ASTM F2101-14). The membrane efficiency will determine if the membrane can meet the required retention and the required R.

Figure 9:
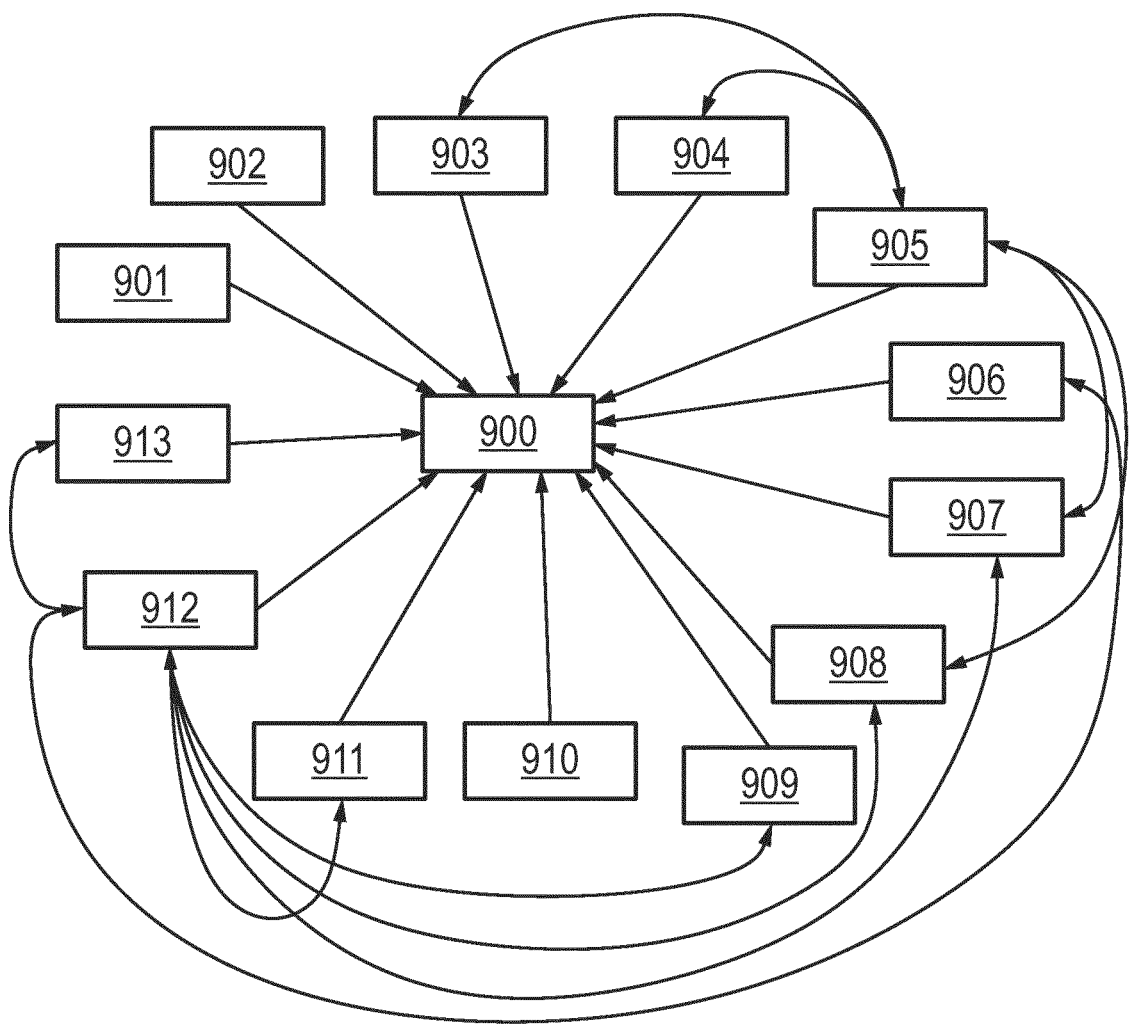
FIG. 9 shows relations between membrane parameters.

Parameters influencing the membrane efficiency 900 are illustrated exemplarily with reference to FIG. 9. There are multiple aspects that influence the membrane efficiency. Several parameters have in turn interdependencies between each other which are indicated by arrows in FIG. 9. For example, the membrane efficiency is influenced by pore size 901, pore shape 902, pore structure 903, membrane and/or composite thickness 904, particle travel distance 905, fiber coating 906, fiber orientation 907, fiber mix 908, fiber shape 909, membrane backing and/or facing layer 910, fiber diameter 911, tribo-electrical parameters 912 as well as the material type 913.

Optionally, the particle speed can be reduced to increase the chance of capturing particles.

Figures 12A, 12B:
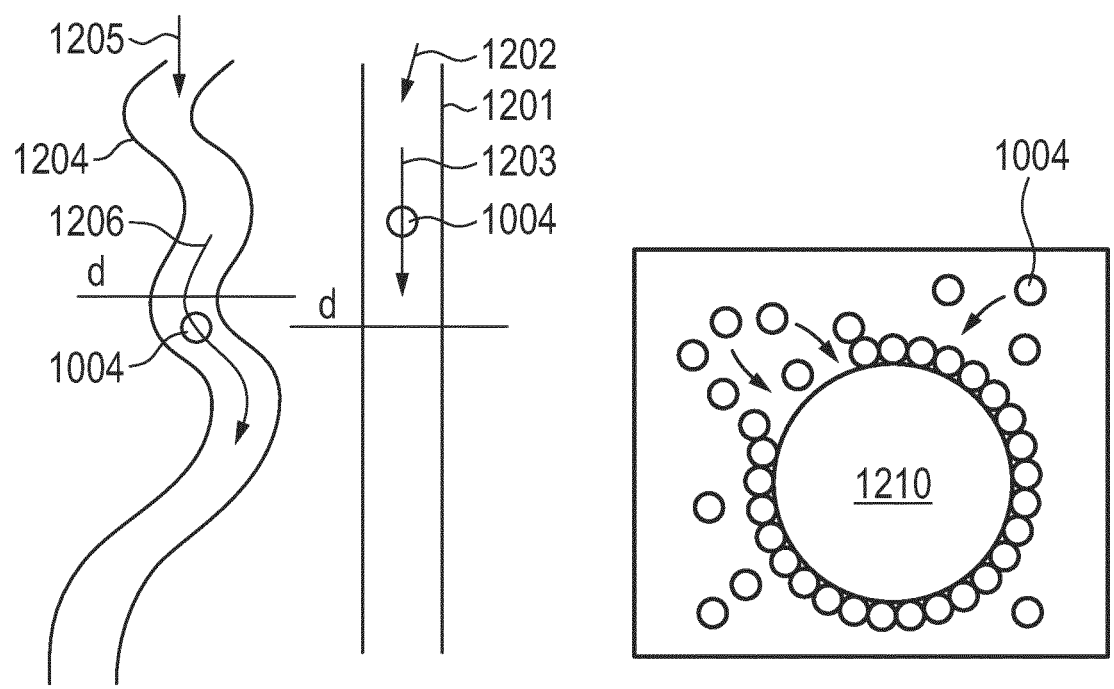
FIGS. 12A and 12B show the impact of membrane parameters on a particle.

Regarding interdependencies, for example the particle travel distance 905 depends on the composite thickness 904, the pore structure 903 as well as fiber mix 908 and fiber orientation 907. As shown in FIG. 12A, a particle 1004 which enters a straight fiber 1201 at 1202 and travels along a straight path 1203 has a shorter travel distance 905 compared to a particle 1004 which enters a curved fiber 1204 at 1205 and travels along a winding path 1206. The longer travel distance along the curved fiber 1204 provides better retention properties compared to the straight fiber 1201. However, there can be a tradeoff between retention and flow resistance.

Figure 10A:
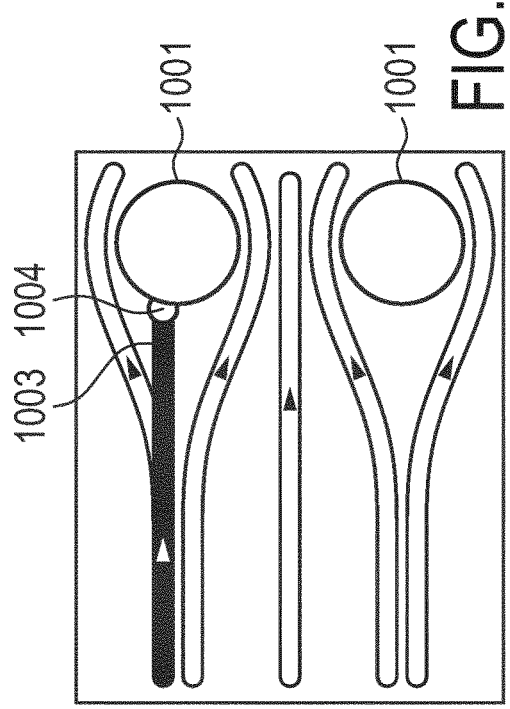
FIG. 10A to 10D show different retention mechanisms.
Figure 10B:
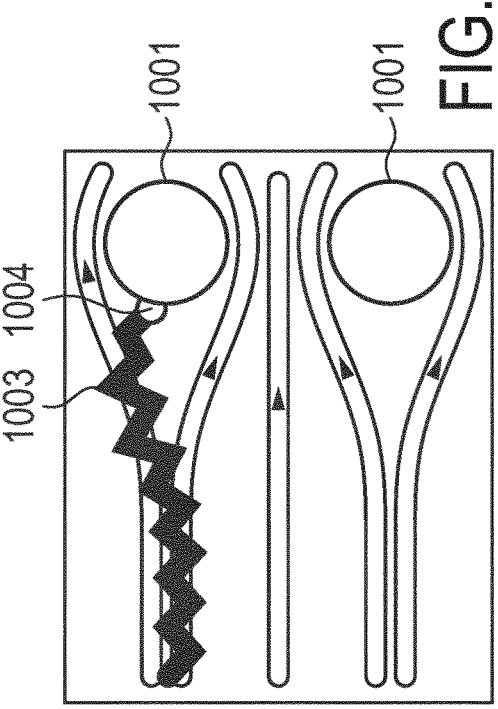
Figure 10C:
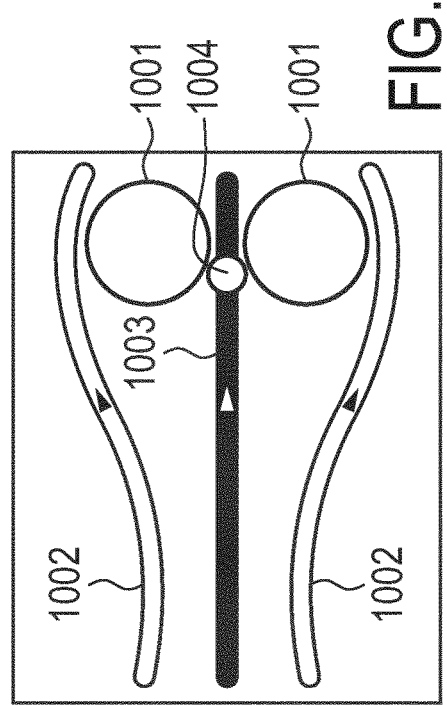
Figure 10D:
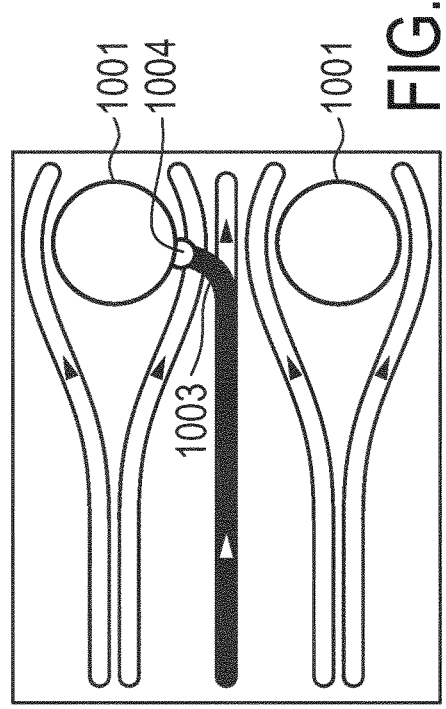

FIGS. 10A to 10D illustrate different retention mechanisms. FIG. 10A illustrates the sieve effect. A particle 1004 travelling along a particle path 1003 cannot pass between fibers 1001 of the membrane and is thus retained whereas an airflow 1002 passes the membrane. FIG. 10B illustrates the inertial mass effect. A particle 1004 travelling along a particle path 1003 is incepted by a fiber 1001 of the membrane. Due to its inertial mass, the particle does not follow the airflow 1002 around the fiber but collides with the fiber 1001. FIG. 10C illustrates the interception effect wherein a particle 1004 travelling along a particle path 1003 is drawn towards the fiber 1001 of the membrane and thereby prevented from passing the membrane. This effect is also exemplarily shown with reference to FIG. 12B. For example, active carbon 1210 is capable of intercepting particles 1004 including gaseous particles and thus prevents them from passing on. FIG. 10D illustrates the diffusion effect. A particle 1004 travels along a corrugated diffuse path 1003, collides with a fiber 1001 of the membrane and does not pass the breathable membrane.

Figure 11:
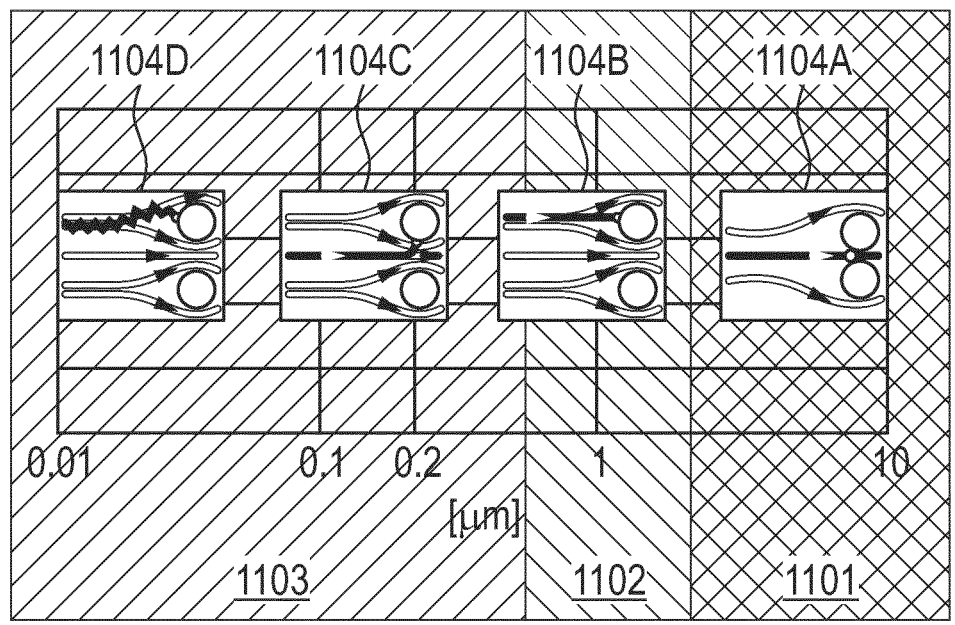
FIG. 11 shows an exemplary relation of retention mechanisms versus particle size.

Depending on the particle size, one or more of the aforementioned retention mechanisms can be combined. FIG. 11 shows an exemplary relation of particle size in [μm] versus the retention mechanisms described with reference to FIGS. 10A to 10D. For example for a range 1101 of coarse membranes the sieve effect 1104A of FIG. 10A can be used. For a range 1102 of fine membranes, the inertial mass effect 1104B of FIG. 10B can be used, whereas for micro filtering 1103 the use of the sieve effect 1104A of FIG. 10C as well as the diffusion effect 1104D of FIG. 1104D have shown good results.

The membrane can be applied as a composite of one or more membranes and optionally one or more supporting layers. A membrane can be provided with a backing and/or facing, in particular a hydrophobic backing and/or facing or as the membrane only. In such a composite, filtration properties can be generated by the one or more same or different membranes and can optionally be further supported by the backing and/or facing.

In conclusion, a breast pump and an expression kit for a breast pump for extracting breast milk from a human teat have been presented. Advantageously, the proposed solution with a hydrophobic breathable membrane for separating the first pressure chamber from the milk path provides a more compact and less expensive expression kit and breast pump, wherein the hygienic function is improved or at least maintained compared with an expression kit using a non-permeable resilient diaphragm.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An expression kit for a breast pump for extracting breast milk from a human teat, the expression kit comprising:
    a breast pump body comprising a first pressure chamber and a second pressure chamber adjacent the first pressure chamber;
    a hydrophobic breathable membrane separating the first pressure chamber and the second pressure chamber, the hydrophobic breathable membrane comprising a hybrid membrane structure comprising both a woven layer and a non-woven layer, the woven layer being liquid-impermeable, wherein the hydrophobic breathable membrane is configured to exchange gas between the first and second pressure chambers and to repel liquid for separating the first pressure chamber from liquid in a milk path, while maintaining a gas volume flow between the first and second pressure chambers; and a restrictor for reducing a surface area of the hydrophobic breathable membrane.

2. The expression kit for a breast pump according to claim 1, wherein the hydrophobic breathable membrane is a bacteria-retentive hydrophobic breathable membrane.

3. The expression kit for a breast pump according to claim 2, wherein the hydrophobic breathable membrane is bacteria-retentive in an aerosol environment.

4. The expression kit for a breast pump according to claim 1, wherein the hydrophobic breathable membrane comprises a hydrophobic backing.

5. The expression kit for a breast pump according to claim 1, wherein the hydrophobic breathable membrane is configured to exchange gas and repel liquid in both directions.

6. The expression kit for a breast pump according to claim 1, wherein at least a portion of the hydrophobic breathable membrane is arranged at an angle with respect to a milk outlet.

7. The expression kit for a breast pump according to claim 1, wherein the hydrophobic breathable membrane comprises one or more of polyethylene, polypropylene, polybutylene terephthalate, polytetrafluoroethylene or expanded polytetrafluoroethylene.

8. The expression kit for a breast pump according to claim 1, further comprising a support structure for supporting the hydrophobic breathable membrane.

9. The expression kit for a breast pump according to claim 1, further comprising a seal arranged between the hydrophobic breathable membrane and the breast pump body.

10. The expression kit for a breast pump according to claim 1, further comprising a wear indicator for indicating a wear of the expression kit, in particular of the hydrophobic breathable membrane.

11. The expression kit for a breast pump according to claim 1, further comprising a splash guard arranged between the milk path and the hydrophobic breathable membrane.

12. The expression kit for a breast pump according to claim 1, wherein at least one of the first pressure chamber and the second pressure chamber is configured to enable access to the hydrophobic breathable membrane.

13. A breast pump for extracting breast milk from a human teat, the breast pump comprising:
the expression kit according to claim 1, and
a pressure unit for generating a pressure.

14. The expression kit for a breast pump according to claim 1, wherein the first pressure chamber is configured for connection to a pressure unit for generating a pressure in the first pressure chamber.

15. The expression kit for a breast pump according to claim 1, wherein the second pressure chamber comprises a breast-receiving funnel, a milk outlet and the milk path from the breast-receiving funnel to the milk outlet.

16. The expression kit for a breast pump according to claim 1, wherein the non-woven layer is bacteria retentive in an aerosol environment.

17. An expression kit for a breast pump for extracting breast milk from a human teat, the expression kit comprising:

a breast pump body comprising a first pressure chamber and a second pressure chamber adjacent to the first pressure chamber;

a hydrophobic breathable membrane separating the first pressure chamber and the second pressure chamber, the hydrophobic breathable membrane comprising a hybrid membrane structure comprising both a woven layer and a non-woven layer, wherein the hydrophobic breathable membrane is gas-permeable and liquid-impermeable when in contact with a liquid in a milk path, thereby separating the first pressure chamber from the liquid in the milk path while continuing to exchange gas with the second pressure chamber, wherein the woven layer is liquid-impermeable; and a restrictor for reducing a surface area of the hydrophobic breathable membrane.

18. An expression kit for a breast pump for extracting breast milk from a human teat, the expression kit comprising:

a breast pump body comprising a first pressure chamber and a second pressure chamber adjacent to the first pressure chamber;

a hydrophobic breathable membrane separating the first pressure chamber and the second pressure chamber, the hydrophobic breathable membrane comprising a hybrid membrane structure comprising both a woven layer and a non-woven layer, wherein the hydrophobic breathable membrane is gas-permeable and liquid-impermeable for separating the first pressure chamber from liquid in a milk path, wherein the woven layer faces the second pressure chamber, and the non-woven layer faces the first pressure chamber, wherein the hydrophobic breathable membrane is gas-permeable and liquid-impermeable for separating the first pressure chamber from liquid in the milk path; and a restrictor for reducing a surface area of the hydrophobic breathable membrane.

* * * * *